United States Patent [19]

Brunk

[11] Patent Number: 4,899,746
[45] Date of Patent: Feb. 13, 1990

[54] SUTURING APPARATUS
[75] Inventor: Bertil E. Brunk, Lake Geneva, Wis.
[73] Assignee: Brunk Industries, Inc., Lake Geneva, Wis.
[21] Appl. No.: 187,573
[22] Filed: Apr. 28, 1988
[51] Int. Cl.[4] ...................... A61B 17/04; A61B 17/06; D05B 1/00
[52] U.S. Cl. .................................... 606/144; 112/169; 606/222
[58] Field of Search ................. 128/340, 339; 112/169

[56] References Cited
U.S. PATENT DOCUMENTS

| 2,327,353 | 8/1943 | Karle | 112/169 |
| 3,344,790 | 10/1967 | Dorner | 112/169 |
| 4,027,608 | 6/1977 | Arbuckle | 128/334 R |
| 4,235,177 | 11/1980 | Arbuckle | 112/169 |
| 4,557,265 | 12/1985 | Andersson | 128/340 |
| 4,621,640 | 11/1986 | Mulhollan et al. | 128/340 |

FOREIGN PATENT DOCUMENTS 18602  9/1908  United Kingdom ................ 128/340

Primary Examiner—Edward M. Coven
Assistant Examiner—Gary Jackson
Attorney, Agent, or Firm—Richard Bushnell

[57] ABSTRACT

A suturing apparatus is disclosed including a handle unit housing an electric motor having an output drive shaft and a head assembly removably connected to the handle unit and drive shaft and comprising a plurality of drive rollers constructed and arranged for supporting and driving a curved needle around a circular path of travel.

6 Claims, 3 Drawing Sheets

SUTURING APPARATUS

BACKGROUND OF THE INVENTION

The present invention relates to suturing and more particularly to a novel apparatus for applying a suture to close a wound or incision.

At the present time it is the general practice to apply sutures with the aid of a hand held needle. Occasions may arise when it is difficult to force the needle through the tissue at the opposite sides of the wound or incision to be closed. Furthermore, when handling the needle, particularly in difficult situations, there is a risk that the doctor may be punctured by the needle. Such an accident would, of course, subject the doctor to the risk of infection.

In an effort to overcome the disadvantages of using the hand held needle, a power-driven suturing apparatus has been suggested as disclosed in U.S. Pat. No. 4,557,265. The present invention contemplates further advantages and improvements over this prior apparatus.

SUMMARY OF THE INVENTION

It is an important object of the present invention to provide a novel power-driven suturing apparatus constructed so that movement of a needle can be controlled easily and accurately.

It is a further object of the present invention to provide a novel apparatus for suturing of the above described type which is constructed so that the needle and parts of the apparatus directly associated with the needle are disposable so as to reduce any possibility of infection.

A more specific object of the present invention is to provide a novel suturing apparatus of the above described type including a handle unit which may contain a motor, a head unit for a needle and quick-disconnect means between the two units for enabling the head unit to be readily removed and replaced.

Another object of the present invention is to provide a novel suturing apparatus of the above described type which may be relatively easily and economically manufactured.

In carrying out the invention it is contemplated that the novel apparatus will include a handle preferably housing a motor having an output drive shaft and a head assembly or unit with a quick-disconnect connection to the handle and drive shaft, which head assembly comprises a housing, a plurality of drive rollers constructed and arranged for supporting and driving the needle in a precisely controlled manner around a circular path of travel, and gear means operatively connectable with the drive shaft for driving the rollers.

BRIEF DESCRIPTION OF THE DRAWINGS

Other objects of the present invention will become apparent from the following description and the accompanying drawings wherein:

FIG. 3 is an enlarged fragmentary sectional view taken along line 3—3 in FIG. 1;

FIG. 4 is an end view of the roller assembly shown in FIG. 3;

DETAILED DESCRIPTION OF A PREFERRED EMBODIMENT

Figure 1:
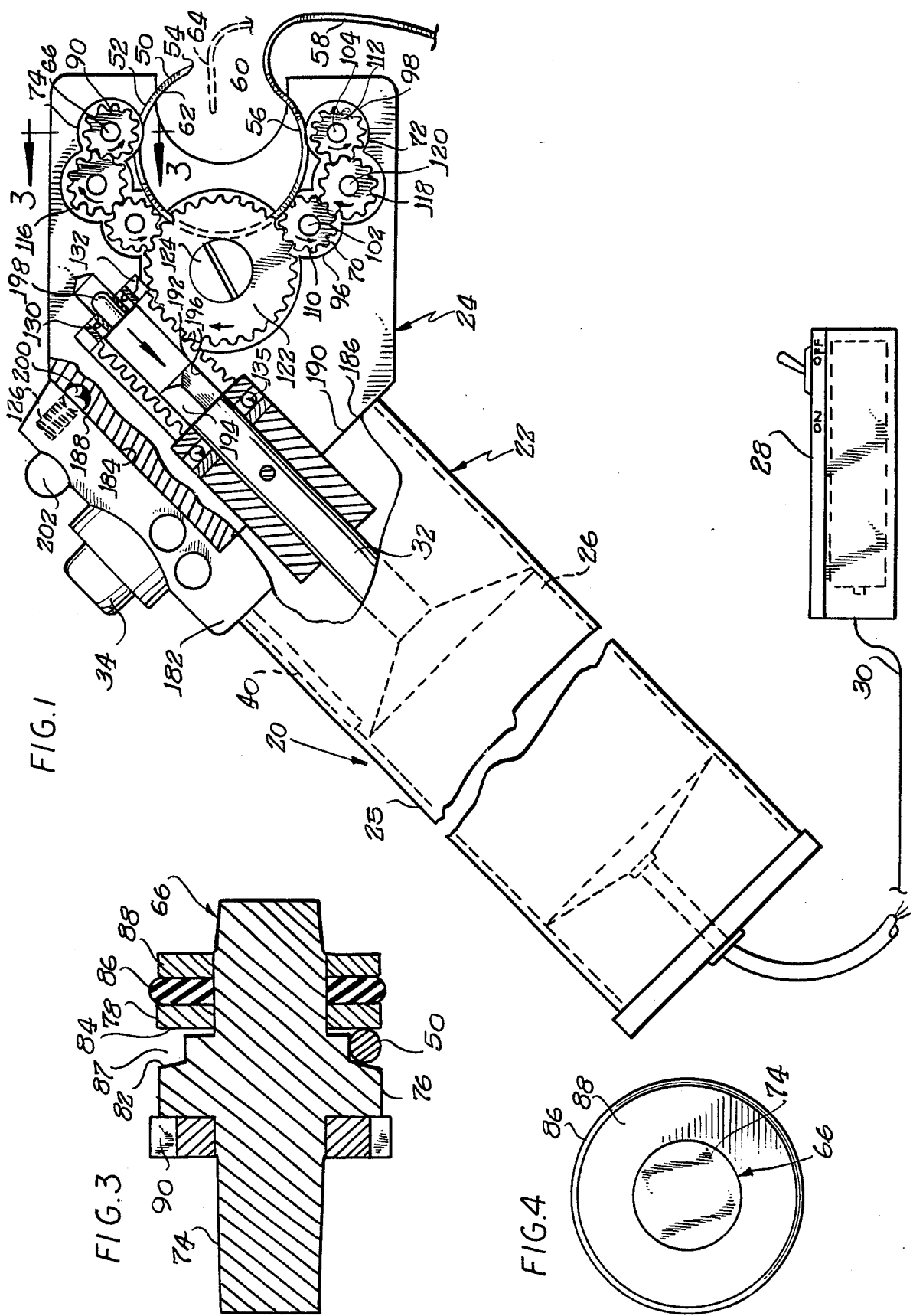
FIG. 1 is a side elevational view, partially broken away, showing an apparatus for suturing incorporating features of the present invention.
Figure 2:
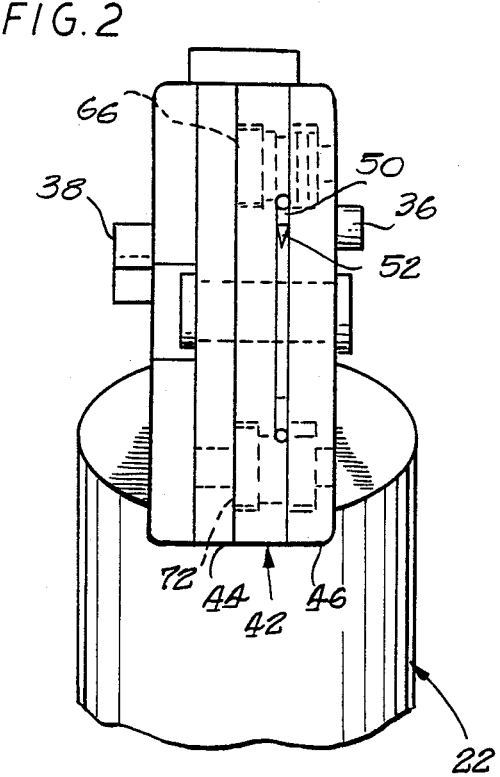
FIG. 2 is an end elevational view of the apparatus as seen from the right hand end of FIG. 1.

Referring now to the drawings wherein like parts are designated by the same reference numerals throughout the various figures, an apparatus 20 incorporating features of the present invention is shown in FIGS. 1 and 2. The suturing apparatus 20 comprises a handle unit 22 and a head unit or assembly 24 described in detail below.

The handle unit 22, in the embodiment shown, includes an elongated tubular case 25 of a size and shape such that it may be easily held in the hand of an operator. A motor 26 of any suitable known construction is mounted within the casing or handle 22. Preferably, the motor is a reversible electric motor connectable to any suitable source of power. In the embodiment shown, a battery pack 28, also of known construction, is connected to the motor 26 by wires 30. The motor 26 has an output or drive shaft 32 extending axially out of the casing for connection with the head assembly in the manner described below.

The handle unit also includes means for controlling the operation of the motor. Preferably the control circuitry has a first push-button switch 34 located on the casing adjacent to the head assembly and adapted to be pressed or actuated to energize the motor to drive the needle continuously as will be hereinafter described. In addition, push-button switches 36 and 38 are mounted on the casing at opposite sides thereof as shown in FIG. 2 for enabling the operator to jog the motor selectively in forward and reverse directions respectively. A printed circuit board 40 or other suitable means containing circuit components of conventional design is mounted in the casing and connected between the motor 26 and the switches 34, 36 and 38 for enabling the operator to control the motor in the manner described.

The head assembly 24 comprises first, second and third housing members 42, 44 and 46 respectively shown in detail in FIGS. 5–7, 8, 9 and 10, 11. The housing members, when assembled as shown in FIGS. 1 and 2 provide a housing adapted to contain means generally designated by the numeral 48 for guiding and driving an arcuate needle 50 around a circular path of travel 52 in the manner to be described. The needle 50 has a pointed forward or leading end 54 and a trailing end 56 with an eye or the like adapted to be connected with a suture thread 58. It is noted that the needle extends in a circle for about 270 degrees and there is a gap 60 between the opposite ends of the needle to enable edges 62 and 64 of tissue to be positioned in the gap for suturing in the manner to be described.

The needle guiding and driving means 48 comprises roller assemblies 66, 68, 70 and 72 spaced around and defining the outer edge of the needle path of travel 52. The roller assemblies 66 through 72 are identical, so that only the assembly 66, which is shown in detail in FIGS. 3 and 4 need be specifically described. The roller assembly 66 includes a shaft 74. An annular drive roller segment 76 is integrally formed with a central portion of the shaft for cooperating with an opposing drive roller segment 78. The drive roller segments combine to define a generally V-shaped groove 80 and present opposing inclined or diversing surfaces 82 and 84 for frictionally engaging opposite side portions of the needle for driving the needle. The roller segment 78 is mounted on the shaft 74 with a slip fit so that it is free to move axially of the shaft. Resilient or spring means in the form of a rubber washer 86 is disposed between the roller segment 78 and a stop or back-up washer 88, which is press-fitted on and non-rotatable relative to the shaft. The dimensions are such that the rubber or spring washer resiliently biases the roller segment 78 for pinching the needle between the surfaces 82 and 84. While the roller segment 78 is axially slidable on the shaft, it is effectively rotatably driven by the shaft through the friction coupling provided by the rubber washer 86 and the back-up washer 88. With the structure just described, the roller is effective for aggressively gripping and frictionally engaging opposite portions of the needle for ensuring accurate and controlled movement of the needle in response to rotation of the roller. A gear 90 is fixed on the shaft 74 by means of a force fit or other suitable device such as key, which gear is adapted to be driven in the manner to be described for driving the roller assembly.

Figure 5:
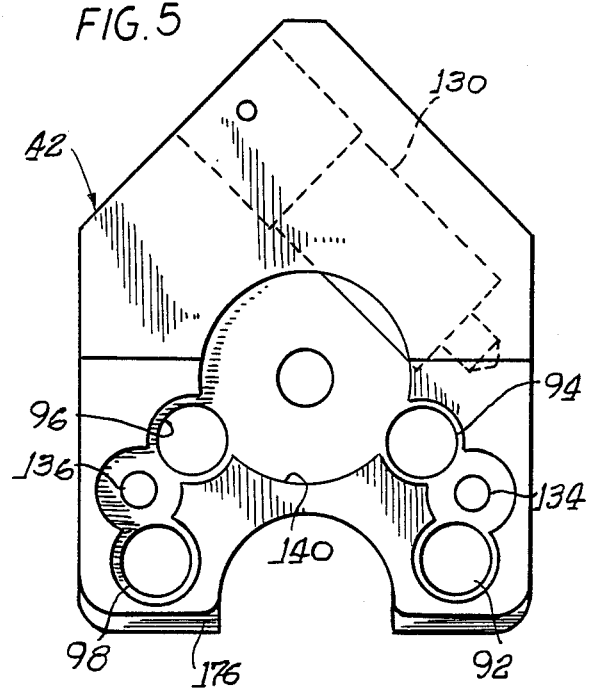
FIG. 5 is a side elevational view of a main housing member of the head assembly included in the apparatus of FIG. 1.
Figure 6:
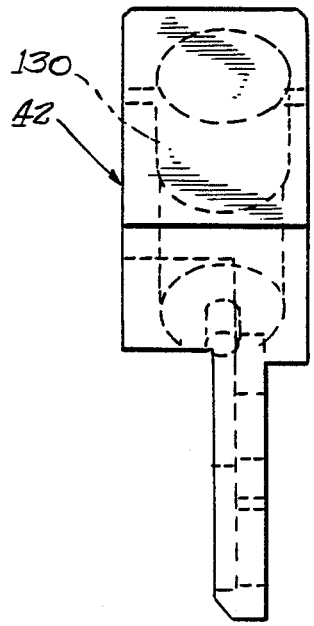
FIG. 6 is an edge view of the housing member as seen from the right hand side of FIG. 5.
Figure 7:
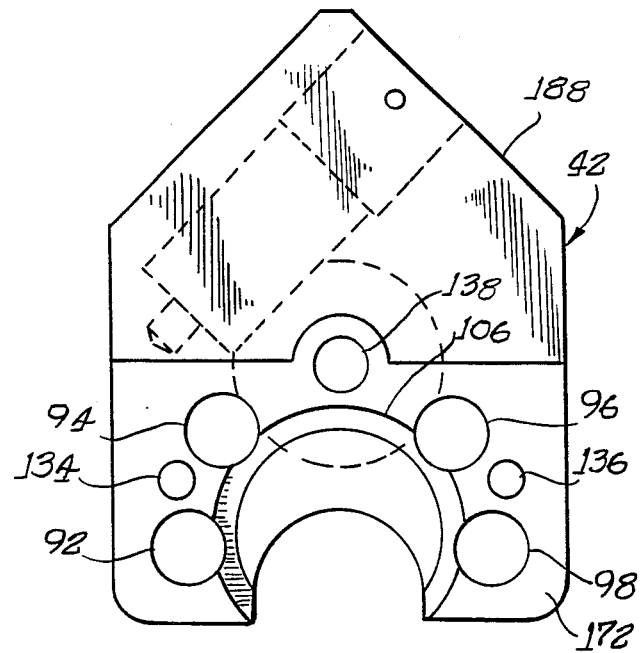
FIG. 7 is a side elevational view of the FIG. 5 housing member as seen from the opposite side.
Figure 8:
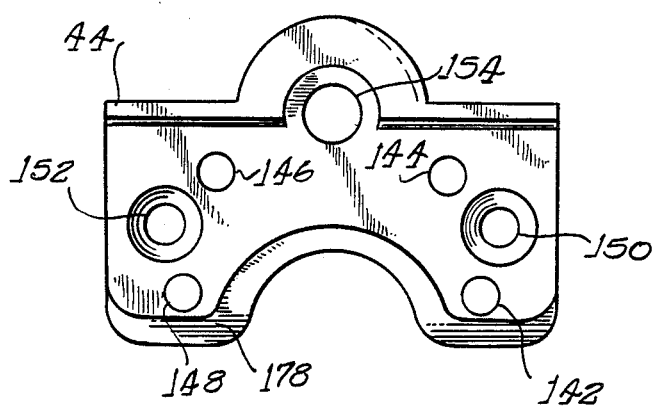
FIG. 8 is a side elevational view of a second housing member of the head assembly.
Figure 9:
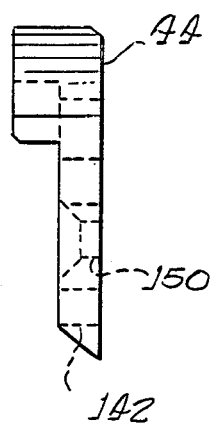
FIG. 9 is an edge view of the FIG. 8 housing member as seen from the right hand side of FIG. 8.
Figure 10:
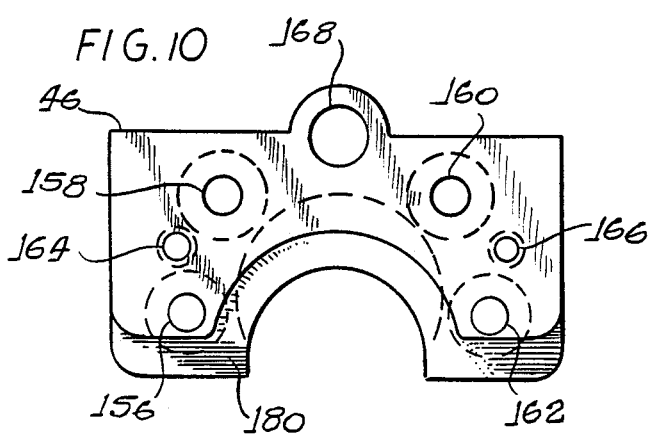
FIG. 10 is a side elevational view of a third housing member of the head assembly of FIG. 1.
Figure 11:
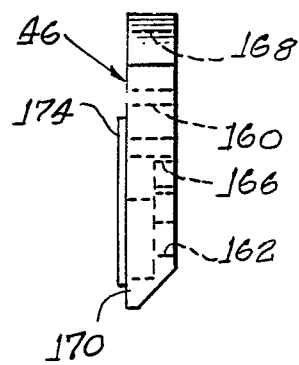
FIG. 11 is an edge view of the FIG. 10 housing member as seen from the left hand side of FIG. 10.

As shown in FIGS. 1, 5, 6 and 7, the first or main housing member 42 of the head assembly is formed with a transverse aperture 92 for receiving the shaft 74 of the roller assembly 66. This head member is provided with additional similar transverse apertures 94, 96 and 98 for accommodating shafts 100, 102 and 104 of the roller assemblies 68, 70 and 72. As previously indicated, the roller assemblies 66 through 72 are positioned for engaging the needle and defining the outer margins of the circular path 52. In addition it is to be noted that the roller assemblies are located and spaced from each other in a manner such that at least three of the rollers are always in supporting and driving engagement with the needle during passage of the point of the needle into and substantially entirely through the tissue being sutured. It is noted that the groove 106 is formed in the wall of the housing number 42 as shown in FIG. 7 to provide clearance for the needle moving around from the path 52. The groove is positioned so that its outer peripheral wall or surface is located radially outwardly of the points of contact between the roller assemblies and the needle, so as to minimize or avoid any frictional contact between the needle and the wall of the groove.

The drive means for the roller assemblies includes not only the gear 90 on the shaft 74, but corresponding gears 108, 110 and 112 on roller shafts 100, 102 and 104 respectively. In addition, an idler gear 114 mounted on shaft 116 meshes with gears 90 and 108 and another idler gear 118 mounted on shaft 120 meshes with gears 110 and 112. A main drive gear 122 mounted on shaft 124 meshes with gears 108 and 110 so that all of the roller assemblies will be precisely driven in unison. The drive gear 122 also meshes with and is driven by a worm gear 126, which is located in a bore 128 formed in the housing member 42. A roller bearing 130 is radially supported on shoulders 132 at an inner end of the bore for a purpose to be described. A thrust bearing 135 is provided in the opposite end of the bore for absorbing the end thrust from the worm gear when the gear is driven in the direction of the arrow (see FIG. 1) for advancing the needle.

Referring again to FIGS. 5-7, it is seen that the housing member 42 has apertures 134 and 136 respectively for receiving the shafts 116 and 120 of the idler gears and another aperture 138 for receiving the shaft 124 of the drive gear 122, disposed in a pocket 140.

Referring particularly to FIGS. 8 through 11 along with FIGS. 5-7, it is seen that the housing members 44 and 46 complement the main housing member 42 so as to provide a complete housing into which the roller assemblies and drive gearing may be readily assembled. Thus housing member 44 is provided with shaft accomodating apertures 142, 144, 146 and 148, adapted to be aligned with the apertures 92, 94, 96 and 98 for receiving ends of the roller assembly shaft. Additional apertures 150 and 152 in the housing member 44 align with the previously described apertures 134 and 136 for receiving ends of the idler gear shaft and aperture 154 aligns with the aperture 138 for receiving an end at the main drive gear shaft.

The supplemental or third housing member 46 is also formed with apertures adapted to receive ends of the various roller and gear shafts projecting from the main housing member. Thus housing member 46 is formed with apertures 156, 158, 160 and 162 adapted to align with the roller shaft apertures 92, 94, 96 and 98 and the main housing member. Additional apertures 164 and 166 in the housing member 46 align with the idler gear shaft apertures 134 and 136 in the main housing member and aperture 168 in the housing member 46 aligns with the main gear drive shaft aperture 138 in the housing member 42.

The housing member 46 has a side surface or face 170 adapted to abut and mate with a side surface 172 on the main housing member 42. As a result, the housing member 46 will cover the groove 106 formed in the main housing member. As shown best in FIG. 9, the housing member 46 includes an arcuate flange 174 projecting from the face 170 for entering the groove 106 and thus closing the inner side of the circular path of travel 52 of the needle. While the flange 174 cooperates with the surfaces of the groove 106 to enclose the needle path of travel, it is contemplated that the needle will be primarily supported as well as driven by the rollers whereby the needle will avoid substantial frictional contact with the stationary surfaces of the housing members which might interfere with the smooth operation of the needle.

Again referring to FIGS. 5-11, it is seen that the housing members 42 and 44 have complementary beveled surfaces 176 and 178, while the opposite side housing member 46 has a corresponding surface 180 so that the overall combination provides the housing or head structure with a tapered edge adjacent to the location where the sutures are to be applied so as to enhance the ability of the doctor to see the exact manner in which the needle is being inserted to suture a wound.

In accordance with a feature the present invention, the head unit or assembly is adapted to be easily and quickly connected and/or disconnected from the handle unit. More specifically, the handle unit has an enlargement or fitting 182 at one end of the case 25, which fitting carries the previously-described switches 34, 36 and 38. In addition, the fitting 182 presents a flat longitudinal surface 184 and a flat transverse surface 186 adapted to mate with and engage complementary flat surfaces 188 and 190 presented by the main housing member 42. These mating surfaces effectively lock the handle unit and the head assembly against relative rotation when the parts are in relationship as shown in FIGS. 1 and 2.

As shown in FIG. 1, drive shaft 32 extends from the case 25 and parallel to the surface 184 for entry into a complementary bore 192 in the worm gear 126. The drive shaft 32 includes a non-circular portion preferably having flat surfaces 194 adapted to engage complementary flat surfaces 196 formed in the wall of the worm-gear bore for providing a driving connection between the shaft 32 and the worm gear. At the outer or free end of the shaft 32 a reduced diameter section 198 is provided for entry into and support by the radial ball bearing 130. While the bearing 130 provides lateral or radial support for the drive shaft and worm gear, the thrust bearing 135 is adapted to accommodate the axial thrust generated by the worm gear when the apparatus is actuated for driving a needle into the tissue to be sutured.

It will be appreciated that the head assembly can be quickly and easily assembled with the handle unit simply by slipping the worm gear over the outer end of the drive shaft 32 until the housing surface 190 engages the surface 186. Preferably a spring-biased ball detent 200 (see FIG. 1) is provided between the fitting 182 and the housing member 42 for releasably retaining the head assembly.

While the operation of the suturing apparatus is apparent from the previous description, a brief summary is as follows. In the first instance a new and sterile head assembly is to be engaged with the handle unit. Then, in the embodiment shown, the battery pack should be switched on. If desired, an indicator light 202 may be provided on the fitting 182 to show when the battery pack is on. Then when the doctor wishes to advance the needle, it is merely necessary to press the switch 34 for continuous operation or the switch 38 for intermittent or jogging operation. When either one of these switches are energized, the drive shaft 32 drives the worm gear which in turn drives the gear 122 and the roller and idler gears in the directions of the arrows in FIG. 1. The combination of the worm gear and drive gear 122 provides for desired high speed reduction so that the needle may be driven at a pace acceptable to the doctor's needs. In addition, the drive gearing, including the worm gear, is self-locking so that whenever the motor is de-energized, the gearing cannot move and the needle will be securely held in a fixed position. In the event it is desired to retract the needle, it is merely necessary for the doctor to depress the reverse switch 38.

It is contemplated that the housing members and drive gearing may be economically fabricated from suitable plastic material so as to minimize the cost of the head assembly and make it practical to discard the assembly after each use. As will be understood, such a disposable head assembly will aid in minimizing the possibility of the spread of infection.

While a preferred embodiment of the present invention has been shown and described herein, it is obvious that many structural details may be changed without departing from the spirit and scope of the appended claims. For example, while a battery has been shown as connected with the motor for providing the power source, it is contemplated that a built-in rechargable battery could be placed in the case 25 or even that the motor could be connected by a suitable cord to a wall outlet. The invention is claimed as follows:

The invention is claimed as follows:

1. An apparatus for suturing comprising a housing and means on said housing for supporting and driving an arcuate needle around a circular path comprising; a plurality of drive rollers spaced along said circular path, speed-reducing gearing including a worm gear having a central bore for receiving a drive shaft, a handle unit including a drive shaft, and means providing a quick-disconnect between said housing and said handle unit and also between said needle driving means and said drive shaft.

2. A suturing apparatus as defined in claim 1, which includes an electric motor mounted in said handle unit and connected with said drive shaft, said motor being connectable with a source of electrical power.

3. A suturing apparatus as defined in claim 2, which includes control switch and circuit means on said handle unit and connected with motor for enabling an operator selectively to energize and de-energize said motor.

4. A suturing apparatus as defined in claim 1, which includes at least three of said drive rollers spaced around said circular path for causing at least two of the drive rollers always to be in supporting and driving engagement with said needle.

5. A suturing apparatus as defined in claim 1, wherein each of said drive rollers comprises opposed surface means for embracing and frictionally engaging opposite side portions of the needle.

6. An apparatus for sutring comprising housing means, means on said housing means defining a circular path, a curved needle having a pointed front end and a trailing end connectable with a suture thread or the like, said curved needle having a length for extending at least 270 degrees and being disposed for movement around said circular path, said means defining said circular path including more than two drive elements for engaging and driving said needle, said drive elements being spaced around said path so that at least two of said drive elements are always in driving engagement with said needle, at least certain of said drive elements comprising roller means having generally V-shaped peripheral grooves presenting opposed sides surfaces for embracing and frictionally engaging opposite sides of the needle, said roller means comprising first and second separate opposite side parts respectively presenting said opposed side surfaces, and means resiliently urging said parts toward each other for biasing said side surfaces against said opposite side portions of said needle and drive means on said housing operatively connectable with a motor for driving said drive elements.

* * * * *